US00PP34182P2

(12) United States Plant Patent
Bacon et al.

(10) Patent No.: US PP34,182 P2
(45) Date of Patent: May 3, 2022

(54) PLUM TREE NAMED 'SUPLUM61'

(50) Latin Name: ***Prunus salicina* x *armeniaca***
Varietal Denomination: SUPLUM61

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/501,815

(22) Filed: Oct. 14, 2021

(51) Int. Cl.
*A01H 5/08* (2018.01)
*A01H 6/74* (2018.01)

(52) U.S. Cl.
USPC ..... Plt./184
CPC ..... *A01H 6/7427* (2018.05)

(58) Field of Classification Search
USPC ..... Plt./184
CPC ..... A01H 6/7427; A01H 5/08
See application file for complete search history.

*Primary Examiner* — Keith O. Robinson
(74) *Attorney, Agent, or Firm* — Knobbe, Martens, Olson & Bear, LLP

(57) ABSTRACT

The new variety 'Suplum61' is characterized by having fruit that is large, with dark red dapple skin as firm flesh, a mildly sweet flavor and a stone that is adherent to the flesh.

1 Drawing Sheet

Latin name of the genus and species claimed: *Prunus salicina* x *armeniaca.*

Variety denomination: 'SUPLUM61'.

BACKGROUND AND SUMMARY OF THE INVENTION

This application relates to the discovery and asexual propagation of a new and distinct variety of plum tree, *Prunus salicina* x *armeniaca* 'Suplum61'. The new variety was first originated by hybridization near Wasco, Kern County, Calif. and identified in September 2018 by Terry A. Bacon and Terrence J. Frett as breeder number 'PC2223RR'.

The seed parent is 'PC1372RP' (unpatented breeding selection), and the pollen parent is 'Suplumfortynine' (U.S. Plant Pat. No. 27,326). The parent varieties were first crossed in March 2015, the date of first sowing being March 2016 and the date of first flowering being March 2018. The new plum variety 'Suplum61' was first asexually propagated by Terry A. Bacon and Terrence J. Frett near Wasco, Kern County, Calif. in February 2019 by dormant grafting.

The new variety 'Suplum61' is characterized by having fruit that is large for an early season plum, with dark-red dapple skin, firm red flesh, a mildly sweet flavor and a stone that is adherent to the flesh.

The new variety 'Suplum61' resembles its seed parent 'PC1372RP' (unpatented breeding selection) in that both have fruit with dark red dapple skin and red flesh. However, flowering time starts 7 days earlier for the new variety 'Suplum61' and the fruit of the new variety 'Suplum61' begins ripening about 16 days earlier than the fruit of 'PC1372RP'. Further, the new variety 'Suplum61' also has a fruit brix of 17% compared to a fruit brix of 15% for 'PC1372RP'.

The new variety 'Suplum61' resembles its pollen parent 'Suplumfortynine' (U.S. Plant Pat. No. 27,326) in that both have fruit with red dapple skin. However, the skin of the fruit of 'Suplum61' is darker than the skin of the fruit of 'Suplumfortynine'. Also, the new variety 'Suplum61' differs from 'Suplumfortynine' in that flowering time starts 6 days earlier for the new variety 'Suplum61' and the fruit of the new variety 'Suplum61' begins ripening about 6 days earlier than the fruit of ' Suplumfortynine'. Further, the new variety 'Suplum61' also has a fruit brix of 17% compared to a fruit brix of 15% for 'Suplumfortynine'.

The fruit of the new variety 'Suplum61' ripens earlier in the season than 'Suplumfortyone' (U.S. Plant Pat. No. 22,430), 'Suplumfiftyeight' (U.S. Plant Pat. No. 33,247), 'Suplumfiftyseven' (U.S. Plant Pat. No. 31,849) and 'Black Splendor' (unpatented), starting on May 15th, compared to May 24th, June 7th, June 17th and Jun 11$^{th}$ for the other varieties, respectively. The new variety 'Suplum61' has red flesh like 'Suplumfortyone', 'Suplumfiftyeight', 'Suplumfiftyseven' and 'Black Splendor'. However, the new variety 'Suplum61' has smaller fruit at 105 g compared to 110 g for 'Suplumfortyone', 132 g for 'Suplumfiftyeight', 140 g for 'Suplumfiftyseven' and 130 g for 'Black Splendor'. Further, the new variety 'Suplum61' has dark-red dapple skin color compared to the black skin of 'Suplumfortyone', 'Suplumfiftyeight', 'Suplumfiftyseven', and 'Black Splendor'. The brix of the new variety 'Suplum61' is 17% and the Brix:Acid ratio is about 26.6 compared to 'Suplumfortyone' with a brix of 15 and a Brix:Acid ratio of 25; 'Suplumfiftyeight' with a brix of 18 and a Brix:Acid ratio of 32; 'Suplumfiftyseven' with a brix of 16 and a Brix:Acid ratio of 31; and 'Black Splendor' with a brix of 14 and a Brix:Acid ratio of 16.

The new variety 'Suplum61' has been shown to maintain its distinguishing characteristics through successive asexual propagations by, for example, cuttings and grafting.

BRIEF DESCRIPTION OF THE PHOTOGRAPH

The accompanying color photographic illustration, FIG. 1, shows typical specimens of the foliage and fruit of the plum variety 'Suplum61'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to three-year-old 'Suplum61' trees grown in the vicinity of Wasco, Kern County, Calif. during 2021 and is believed to apply to plants of the variety grown under similar conditions of soil and climate elsewhere.

TREE

General: (Measurements taken on three-year-old trees unless otherwise noted).

- *Size.*—Medium: reaches a height of approximately 3 meters with normal pruning.
- *Habit.*—Spreading.
- *Vigor.*—Medium. Top shoot growth of 1 meter during the growing season.
- *Productivity.*—Very productive. About 700 25 lb cartons per acre. Fruit set is usually two or more times desired amount for marketable size fruit. Thinning and spacing of fruit is necessary.
- *Bearer.*—On spurs and long shoots.
- *Fertility.*—Self-incompatible; requires pollinator.
- *Hardiness.*—Hardy in all fruit growing areas of California. Winter chilling requirement is approximately 350 hours at or below 7.2° C.
- *Disease resistance/susceptibility.*—Under close observation in Kern County, Calif., no particular plant/fruit disease resistance/susceptibility has been observed.
- *Insect resistance/susceptibility.*—Under close observation in Kern County, Calif., no particular plant/fruit insect resistance/susceptibility has been observed.

Trunk: (Measurements taken at approximately 30 cm above soil line on mature tree).

- *Diameter.*—Approximately 14 cm.
- *Texture.*—Medium shaggy, increasing with age of tree.
- *Trunk color.*—About Medium Greyed-Green 198B with highlights of Dark Greyed-Orange 166A, becoming darker with age.

Branches: (Measurements taken at approximately 90 cm above soil line).

- *Size.*—Diameter approximately 10 cm.
- *Texture.*—Medium shaggy, increasing with age.
- *Color.*—About Dark Grey 201B with highlights of about Medium Grey-Brown 199B, becoming darker with age.
- *Lenticels.*—Present.
- *Lenticels density.*—Plentiful, about 50/cm$^2$.
- *Lenticels color.*—About Medium Greyed-Green 197C.
- *Lenticels dimensions.*—Length: approximately 1-3 mm. Width: approximately 0.5 mm.

One year old shoots: (Data taken in September at mid-point of current-season growth).

- *Size.*—Average diameter approximately 7 mm.
- *Topside color.*—About Medium Green 137C, becoming Medium Greyed-Orange 165B by September.
- *Underside color.*—About Medium Green 137C, becoming Medium Greyed-Orange 165B by September.
- *Internode length.*—Approximately 20 mm. Midway on shoot.
- *Lenticels color.*—About Medium Greyed-Green 197C.
- *Lenticels size.*—Very small, difficult to see, about 0.2 mm diameter.
- *Lenticels density.*—Medium.
- *Spur length.*—Medium, usually 8 mm.
- *Anthocyanin intensity on upper side of shoot.*—Medium.

Vegetative buds:

- *Position of vegetative bud in relation to shoot.*—Slightly held out.
- *Size.*—Medium, approximately 1.7 mm wide×2.7 mm long.
- *Shape.*—Ovoid.
- *Bud shape at apex.*—Obtuse.
- *Color.*—About Dark Greyed-Orange 166A.

Flower buds:

- *Shape.*—Ovoid.
- *Dimensions.*—Approximately 1.1 mm wide×2 mm long.
- *Color.*—About Medium Greyed-Orange 177B.
- *Distribution.*—2-6 buds, generally on spurs and one-year old shoots.
- *Ratio of flowering buds to vegetative buds.*—2-6 flower buds to 1 vegetative bud.

FOLIAGE

Leaves: (Data taken in July on fully expanded leaves at mid-point of the current season growth).

- *Average length.*—Medium; approximately 7.4 cm without petiole.
- *Average width.*—Medium; approximately 3.9 cm.
- *Length/width ratio.*—Moderately elongated; about 1.8:1.
- *Shape.*—Elliptic.
- *Color.*—Upper surface: About Dark Green 139A. Lower surface: About Medium Green 136C.
- *Glossiness of upper side.*—Medium.
- *Angle at apex (excluding tip).*—Acute.
- *Shape of base.*—Cuneate.
- *Vein color.*—About Light Green 139D with highlights of Medium Greyed-Orange 176C where exposed to sun.
- *Venation.*—Pinnately net veined.
- *Surface texture.*—Smooth on both upper and lower surfaces.
- *Shape in the cross section.*—Concave.
- *Profile.*—Up folded.
- *Leaf blade tip.*—Curved downwardly.
- *Undulation of margin.*—Slight.
- *Density of pubescence of lower side.*—Absent or very sparse.
- *Incisions of margin.*—Bi-crenate.

Petiole:

- *Average length.*—Long, approximately 15 mm.
- *Average diameter.*—Approximately 2 mm.

*Color.*—About Light Green 139D with highlights of Medium Greyed-Orange 176C where exposed to sun.

Stipules:

*Number/leaf bud.*—Usually one.

*Typical length.*—Approximately 6 mm.

*Color.*—About Dark Greyed-Orange 166A when dried.

*Persistence.*—Falls off.

Leaf glands:

*Average number and arrangement.*—2-4, alternating. Predominately on petiole.

*Form.*—Globose.

*Diameter.*—Approximately 0.3 mm.

*Color.*—About Medium Greyed-Yellow 162A becoming Dark Greyed-Orange 166A over time.

*Positions of nectarines (glands).*—Rarely present, but predominately on petiole when found.

FLOWERS

General:

*Time of beginning of flowering.*—Early for the San Joaquin Valley, Calif.

*Flower blooming period.*—First bloom: Approximately February 16 in Wasco, Calif. Full bloom: Approximately February 20 in Wasco, Calif.

*Location of first bloom.*—Tips of one-year old shoots.

*Location of full bloom.*—Central part of the tree canopy.

*Duration of bloom.*—Approximately 10 days.

*Flower diameter.*—Medium, approximately 1.8 nm.

*Flower form.*—Showy.

Pedicels:

*Length.*—Long, approximately 12 mm.

*Diameter.*—Approximately 1.2 mm.

*Color.*—About Light Green 138C.

*Pubescence.*—Absent.

Petals:

*Number.*—5.

*Arrangement.*—Slightly overlapping.

*Color.*—About White 155A.

*Length.*—Medium, approximately 7.8 mm.

*Width.*—Approximately 7.9 mm.

*Shape.*—Circular.

*Apex shape.*—Rounded.

*Base shape.*—Narrows at point of attachment.

*Surface texture.*—Smooth.

*Undulation of margins.*—Medium.

*Frequency of flowers with double petals.*—None.

*Claw.*—Absent.

Sepals:

*Number.*—5.

*Length.*—Approximately 4 mm.

*Width.*—Approximately 3 mm.

*Shape.*—Triangular.

*Color.*—About Light Green 138C.

*Surface texture.*—Smooth.

*Margins.*—Undulating.

*Positioning.*—Adpressed to petals.

*Frequency of flowers with double sepals.*—None.

Stamens:

*Number.*—About 24-30; usually 28.

*Average length.*—Variable, ranging from 3 mm to 10 mm.

*Filament color.*—About White 155A.

*Flower pollen color.*—About Light Yellow-Orange 18A.

*Position.*—Perigynous.

Pistil:

*Average length.*—Approximately 3-4 mm.

*Ovary diameter.*—Approximately 2.2 mm.

*Pubescence.*—Absent.

*Stigma extension in comparison to anthers.*—Usually below.

*Style frequency of supplementary pistils.*—Few.

Receptical:

*Depth.*—Medium, approximately 4 mm.

*Pubescence of inner surface.*—Absent.

*Pubescence of outer surface.*—Absent.

FRUIT

General: (Description taken at firm-mature near Wasco, Kern County, Calif.).

Ripening:

*Time of beginning of fruit ripening.*—Very early season.

*Date of first pick.*—Approximately May 15.

*Date of last pick.*—Approximately May 25.

Size:

*Height.*—Medium, approximately 62 mm.

*Diameter in line with suture plane.*—Approximately 57 mm.

*Diameter perpendicular to suture plane.*—Broad, approximately 61 mm.

*Average weight.*—Large, approximately 105 gm.

Peduncle:

*Length of stem.*—Short, approximately 7 mm.

*Diameter of stem.*—Approximately 3 mm.

*Color of stem.*—About Light Green 139D.

Shape:

*Viewed from apex.*—Circular.

*Viewed in-line with suture.*—Circular.

*Viewed from side, perpendicular to suture.*—Circular.

*Symmetry.*—Symmetric or slightly asymmetric.

*Shape of base.*—Pointed.

*Shape of apex.*—Rounded.

Fruit stem cavity:

*Depth of stalk cavity.*—Shallow; Approximately 5 mm.

*Width of stalk cavity.*—Medium; Approximately 12 mm.

*Depth of suture.*—Absent or very shallow.

Fruit skin:

*Thickness.*—Medium, typical of most varieties.

*Flavor.*—Mildly tart.

*Adherence to flesh.*—Strong.

*Surface texture.*—Slight rippled.

*Pubescence.*—None.

*Bloom on skin.*—Strong.

*Ground color.*—Not visible.

*Overcolor.*—About Dark Black 187A.

*Relative area of overcolor.*—Whole surface.

*Pattern of overcolor.*—Solid.

*Reticulation.*—Present.

*Tendency to crack.*—Rare.

*Number of lenticels.*—Medium, about 10/cm$^2$.

*Size of lenticels.*—Very small, approximately 0.2 mm.

Flesh at firm-mature harvest stage:

*Ripens.*—Evenly.

*Texture.*—Crisp-juicy.

*Flavor.*—Mildly sweet, medium acid, about 26.6 Brix: Acid.
*Color.*—About Dark Red 45A.
*Firmness.*—Firm; typically 10 lb pressure at harvest.
*Juice.*—Medium, able to squeeze free juice easily.
*Acidity.*—Medium; 0.64% titratable acidity.
*Sweetness.*—High; about 17% Brix at harvest.
*Adherence to stone.*—Adherent.
*Amount of fiber.*—Medium.

Fruit use: Fresh market.

Fruit shipping and keeping characteristics: Excellent storage and shipping quality for 6 weeks without shrivel or softening.

Stone:
*Stone freeness.*—Cling.
*Stone size.*—Size: Medium. Length: Approximately 23 mm. Diameter in line with suture plan: Approximately 15 mm. Diameter perpendicular to suture plane: Approximately 9 mm.
*Color.*—About Medium Greyed-Orange 170B when dried.
*Position of maximum diameter.*—Middle.
*Shape from lateral view.*—Narrrow elliptic.
*Shape from ventral view.*—Narrow elliptic.
*Shape from basal view.*—Narrow elliptic.
*Base shape.*—Nearly straight.
*Apex shape.*—Pointed.
*Stone ridges.*—Rounded throughout.
*Stone outgrowing keel.*—Partially developed.
*Ventrical edge.*—Thin with slight wing throughout.
*Dorsal edge.*—Narrow, shallow grooves throughout.
*Fibers.*—Not visible.
*Symmetry in lateral view.*—Symmetrical or slightly asymmetrical.
*Texture of lateral surface.*—Slightly rough.
*Width of stalk-end.*—Broad.
*Tendency to split.*—Rare.

What is claimed is:

1. A new and distinct variety of plum tree named 'Suplum61' as herein described and illustrated.

* * * * *

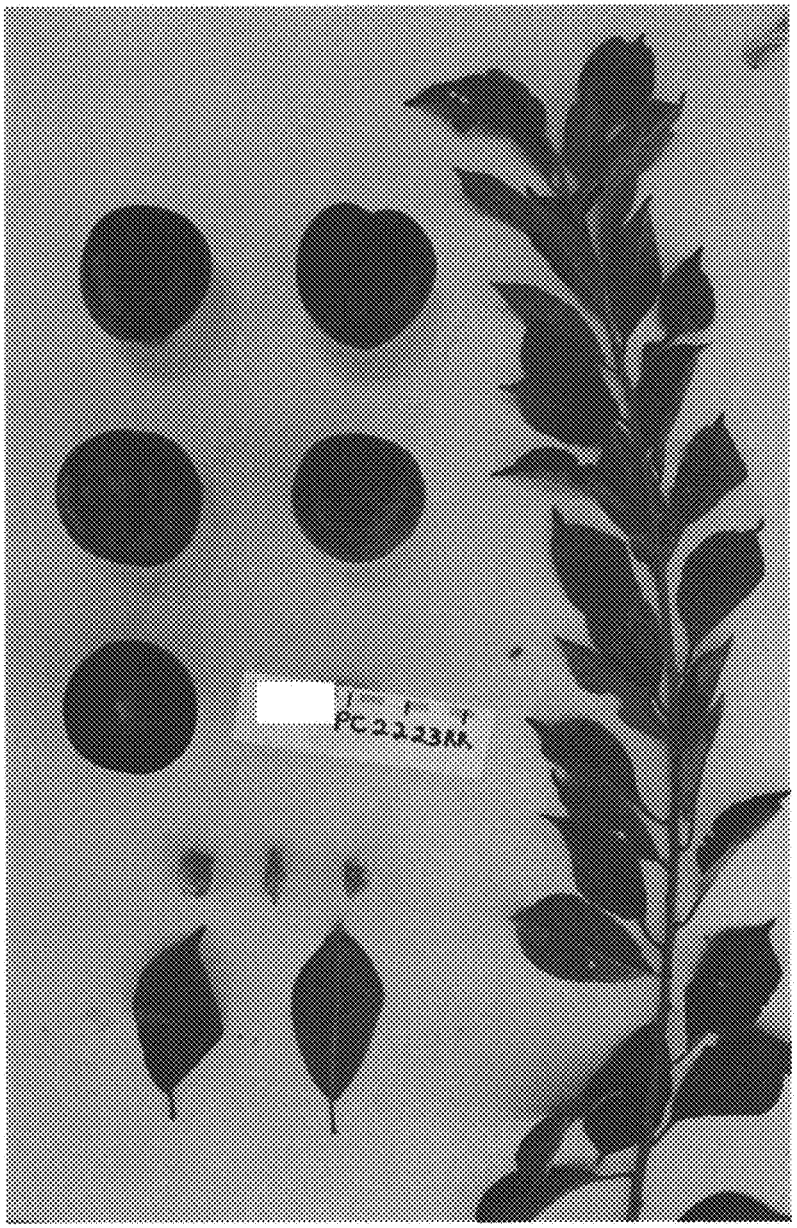
PC2223BK